United States Patent
Nickolson et al.

[11] 4,033,995
[45] July 5, 1977

[54] D-HOMO STEROIDS

[75] Inventors: Robert C. Nickolson; Ulrich Kerb; Rudolf Wiechert, all of Berlin, Germany

[73] Assignee: Schering Aktiengesellschaft, Berlin & Bergkamen, Germany

[22] Filed: Sept. 2, 1975

[21] Appl. No.: 609,707

[30] Foreign Application Priority Data

Sept. 4, 1974 Germany ............... 2442616

[52] U.S. Cl. .................. 260/468.5; 195/51 A; 195/51 S; 260/348 A; 260/408; 260/410; 260/488 B; 260/514.5; 260/586 E; 424/305; 424/311; 424/312; 424/317
[51] Int. Cl.$^2$ .................. C07J 63/00
[58] Field of Search ........ 260/468.5, 488 B, 514.5; 424/305, 311, 317

[56] References Cited
OTHER PUBLICATIONS
Chem. Abstracts, 80:37392g, 37394j.

*Primary Examiner*—Vivian Garner
*Attorney, Agent, or Firm*—Millen & White

[57] ABSTRACT

D-Homo-21-carboxylic acids of the formula

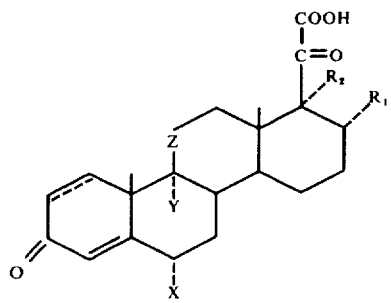

the === represents a single bond or a double bond;
X is a hydrogen atom, a fluorine atom, or methylene;
Y is a hydrogen atom, a fluorine atom, or a chlorine atom;
Z is methylene, carbonyl, $\beta$-hydroxymethylene, a $\beta$-alkanoyloxymethylene or when Y is a chlorine atom, also $\beta$-fluoromethylene or $\beta$-chloromethylene;
$R_1$ is a hydrogen atom or methyl; and
$R_2$ is a hydrogen atom, hydroxy or alkanoyloxy; and their physiologically acceptable salts with bases and the 21-esters thereof, possess topical anti-inflammatory activity.

20 Claims, No Drawings

D-HOMO STEROIDS

BACKGROUND OF THE INVENTION

This invention relates to novel, pharmacologically active D-homo steriods, to processes for their production, and to pharmaceutical compositions containing them.

In German Unexamined Laid-Open Application DOS 2,204,361, 20-oxopregnan-21-oic acid derivatives are described which differ from the D-homo steriods of general Formula I essentially in that they have no D-homo ring. See also U.S. Pat. No. 3,875,194 and Application Ser. No. 284,710, filed Aug. 30, 1972 cited therein, whose disclosures are incorporated by reference.

SUMMARY OF THE INVENTION

The novel D-homo steriods of this invention are those of general Formula I

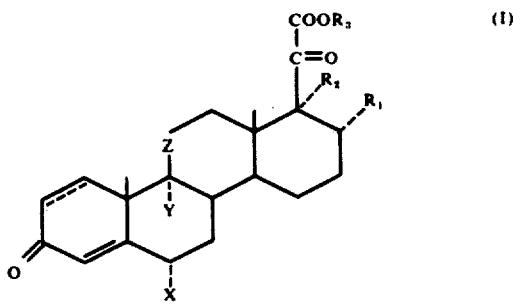

wherein
the === represents a single bond or a double bond;
X is a hydrogen atom, a fluorine atom, or methylene;
Y is a hydrogen atom, a fluorine atom, or a chlorine atom;
Z is a methylene, carbonyl, $\beta$-hydroxymethylene, $\beta$-alkanoyloxymethylene, or when Y is a chlorine atom, also $\beta$-fluoromethylene or $\beta$-chloromethylene;
$R_1$ is a hydrogen atom or methyl;
$R_2$ is a hydrogen atom, hydroxy or alkanoyloxy; and
$R_3$ is a hydrogen atom, the cation of a physiologically acceptable base, or the esterified radical of a physiologically acceptable alcohol.

In another composition aspect this invention relates to pharmaceutical compositions comprising an antiinflammatorily effective amount per unit dosage of at least one D-homo steriod of this invention in admixture with a pharmaceutically acceptable carrier.

In process aspects, this invention relates to processes for the production and use of the D-homo steriods.

DETAILED DISCUSSION

Examples of alkanoyl when Z is $\beta$-alkanoyloxymethylene and when $R_2$ is alkanoyloxy are preferably those of a straight-chain alkanoic acid, i.e., an n-alkanecarboxylic acid, e.g., of 1–8 carbon atoms, e.g., formic acid, acetic acid, propionic acid, butyric acid and caproic acid.

Because activity resides in the D-homo pregnanoic acid steriodal structure, $-COOR_3$ can also represent any ester group, but preferably $R_3$ is hydrocarbon.

Examples of contemplated classes of compounds of this invention are those wherein:

1a: $R_3$ is H;
1b: $R_3$ is alkyl of 1–4 carbon atoms, preferably $CH_3$, $C_2H_5$, $n-C_3H_7$ or $n-C_4H_9$;
1c: $R_1$ is H; especially those of (a) and (b);
1d: $R_1$ is $CH_3$; especially those of (a) and (b);
1e: $R_2$ is OH; especially those of (a) and (b);
1f: $R_2$ is H; especially those of (a), (b), (c) and (d);
1g: === is a double bond, especially those of (b), (c), (d), (e) and (f);
1h: === is a single bond, especially those of (b), (c), (d), (e) and (f);
1i: Z is $\beta$-hydroxymethylene, especially those of (b), (c), (d), (e), and (f);
1j: Z is carbonyl, especially those of (b), (c), (d), (e) and (f);
1k: Z is methylene, especially those of (b), (c), (d), (e) and (f).

Examples of $R_3$ when that group is a cation of a physiologically acceptable base are those of alkali metals, e.g., sodium potassium, and of ammonia. Contemplated equivalents are salts of other non-toxic metals, e.g., alkaline earth metals, and of amines.

Because activity resides in the D-homo-pregnanoic acid steriodal structure, $-COOR_3$ can also represent any ester group. For example, $R_3$ can be any hydrocarbon group derived from a reaction alcohol of 1–18, preferably 1–12, carbon atoms. The hydrocarbon group can be aliphatic, e.g., alkyl, or cycloaliphatic, preferably monocyclic or aralkyl.

Examples of aliphatic $R_3$ groups are straight and branched chain alkyl of 1–12, preferably 1–8, more preferably 1–4 carbon atoms, e.g., methyl, ethyl propyl, isopropyl, n-butyl, sec.-butyl, tert.-butyl, amyl isoamyl, tert.-amyl, hexyl, heptyl, octyl, decyl, dodecyl, tetradecyl and hexadecyl.

Examples of cycloalkyl are those containing 3–12, preferably 5 or 6 ring carbon atoms, e.g., cyclopropyl, cyclopentyl, cyclohexyl, cyclohexyl-methyl, cyclopentenyl, cyclopentadienyl and p-dicyclohexyl.

Examples of aryl are mono and dicyclic of up to 12 carbon atoms, e.g., phenyl, $\alpha$-naphthyl and $\beta$-naphthyl and p-diphenyl.

Examples of alkaryl are tolyl, xylyl, ethylphenyl and sym-diethylphenyl. Examples of aralkyl are benzyl, phenylethyl and $\alpha$-phenylpropyl and diphenylmethyl.

It will be apparent to those skilled in the art that equivalents of unsubstituted $R_3$ hydrocarbon groups are hydrocarbon groups bearing 1,2,3 or more simple substituents, preferably one, since such substituents ordinarily do not affect the overall activity of the parent pregnanoic acid. Examples of such simple substituents are hydroxy; lower alkoxy, e.g., methoxy, ethoxy, propoxy, butoxy and tert.-butoxy, free or esterified carboxyl and the sodium and potassium salts thereof, and amino groups and their salts, including $NH_2$, mono- and di-lower-alkylamino groups, e.g., methylamino, dimethylamino, ethylamino, diethylamino, propylamino, and butylamino group and the salts thereof.

Preferred salts of the amino, mono-lower-alkylamino or di-lower-alkylamino groups include the hydrochlorides, hydrobromides, sulfates, phosphates, oxalates, maleates and tartrates.

Specific examples of such substituted $R_3$ groups are: methyl, carboxymethyl, ethyl, 2-hydroxyethyl, 2-methoxyethyl, 2-aminoethyl, 2-dimethylaminoethyl, 2-carboxyethyl, propyl, allyl, cyclopropylmethyl, isopropyl, 3-hydroxypropyl, propinyl, 3-aminopropyl, butyl, sec.-butyl, tert.-butyl, 2-butyl, cyclobutyl, pentyl, isopentyl, tert.-pentyl, 2-methylbutyl, cyclopentyl, hexyl, cyclohexyl, cyclohex-2-enyl, cyclopentylmethyl, heptyl, benzyl, 2-phenylethyl, octyl, bornyl, isobornyl, menthyl, nonyl, decyl, 3-phenylpropyl, 3-phenylprop-2-enyl, dodecyl, tetradecyl, hexadecyl, and octadecyl.

In process aspect, this invention relates to a process for the production of such novel D-homo steriods wherein:

a. a compound of general Formula II

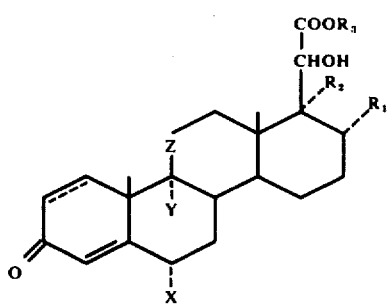

wherein ===, X, Y, Z, $R_1$, $R_2$, and $R_3$ have the values given for Formula I, is oxidized with an oxidizing heavy metal oxide; or b. a compound of general Formula III

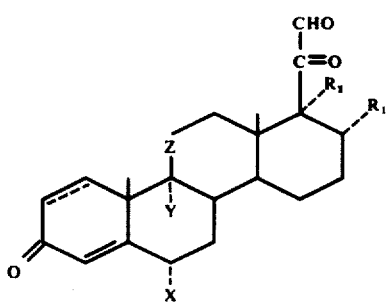

wherein ===, X, Y, Z, $R_1$, and $R_2$ have the values given for Formula I, or hydrates, or acetal thereof, is oxidized in the presence of an alcohol with an oxidizing heavy metal oxide or with atmospheric oxygen; or c. a D-homo steroid of general Formula I saturated in the 1,2-position (=== is a single bond) is dehydrogenated to produce a 1,4-D-homo steroid of general Formula I, or d. the $9\beta$, $11\beta$-epoxy group of an epoxide of general Formula IV

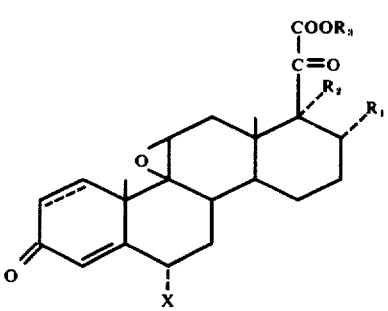

wherein ===, X, $R_1$, $R_2$, and $R_3$ have the above values given for Formula I, is opened with hydrogen fluoride or hydrogen chloride to give a D-homo steroid of general Formula I wherein Z is $\beta$-hydroxymethylene and Y is a fluorine or chlorine atom; or e. a compound of general Formula V

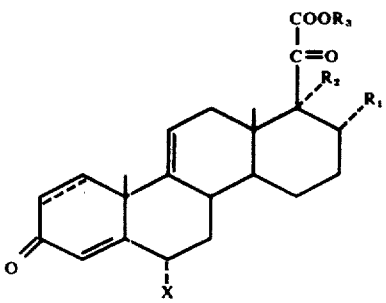

wherein ===, X, $R_1$, $R_2$, and $R_3$ have the values given above for Formula I, is reacted with hypochlorous acid, chlorine, or a mixture of fluorine and chlorine to give a D-homo steroid of general Formula I wherein Y is a chlorine atom; and optionally thereafter, a hydroxy group present in the 11-position is oxidized to a keto group, or an ester of general Formula I is reacted in the presence of a basic catalyst with an alcohol to give the desired final ester by transesterification, or is saponified and optionally thereafter reesterified to a desired final ester.

German Unexamined Laid-Open Application 2,204,361 discloses that pregnanoic acid derivatives with a five-membered D-ring can be produced from the corresponding 20-hydroxypregnan-21-oic acid derivatives by oxidizing the latter in an inert solvent with an oxidizing heavy metal oxide, such as, for example, manganese (IV) oxide or lead (IV) oxide. It can be seen from the description and the examples in DOS 2,204,361 that there is no necessity for maintaining the specific reaction conditions during the oxidation method disclosed in this reference.

The novel D-homo steroids of general Formula I can also be produced from the corresponding 20-hydroxy compounds of general Formula II by oxidizing these compounds in accordance with process variation (a) in an inert solvent with an oxidizing heavy metal oxide, e.g., manganese (IV) oxide or lead (IV) oxide. However, when conducting this reaction, it is necessary to make certain by an exact control of the reaction conditions that only the amount of oxidizing agent is consumed which is necessary for that reaction, because the thus-formed D-homo steroids of general Formula I, in contrast to the conventional pregnanoic acid derivatives, are in most cases of low stability under the employed reaction conditions, and are very readily oxidatively cleaved to the corresponding compounds of the general Formula VI

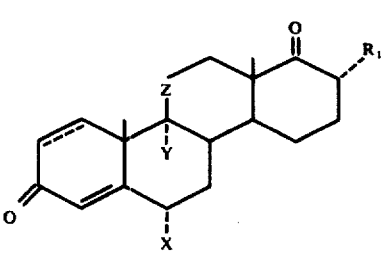

The process according to variation (a) can be conducted in inert solvents conventionally employed in oxidations in the steroid chemistry. Suitable solvents are, for example, hydrocarbons, such as cyclohexane, benzene, toluene, or xylene; chlorinated hydrocarbons, such as methylene chloride, chloroform, carbon tetrachloride, tetrachloroethylene, or chlorobenzene; ketones, such as acetone, methyl ethyl ketone, methyl isobutyl ketone, or acetophenone; or preferably ethers, such as diethyl ether, diisopropyl ether, dibutyl ether, tetrahydrofuran, dioxane, or glycol dimethyl ether; and/or alcohols, such as methanol, ethanol, isopropanol, or tert.-butanol. The process of this invention can also be conducted in mixtures of the aforementioned solvents.

The process according to the invention as disclosed in variation (a) can be conducted, for example, using manganese (IV) oxide or lead (IV) oxide. Preferably, active manganese (IV) oxide is used for this variation of the process, as is conventional in steroid chemistry for oxidation reactions.

The reaction according to variation (a) takes place preferably at a reaction temperature of from 0° to 50° C.

To ensure that only the amount of manganese (IV) oxide or lead (IV) oxide required for the oxidation is consumed, it is suitable to withdraw in a preliminary experiment samples from the reaction mixture at various time intervals, examine these samples analytically, e.g., by means of thin-layer chromatography, and thus determine the optimum reaction time, which is very dependent on the structure of the 20-hydroxy compounds employed. Normally the reaction time is 5-30 minutes when the reaction is conducted at room temperature.

It is also possible to determine by preliminary experiments how much lead (IV) oxide or active manganese (IV) oxide is necessary for the desired oxidation.

The starting compounds of process variant (a) can be prepared from the corresponding 21-hydroxy-20-oxopregnane derivatives. For this purpose, these latter compounds are dissolved in an alcohol, the solution is combined with copper (II) acetate, and the reaction mixture is agitated for several days at room temperature. Then, the mixture is combined with aqueous ammonia, extracted, e.g., with methylene chloride, the organic phase is washed with water, dried, and concentrated under vacuum. A crude product is thus obtained consisting of a mixture of the 20α- and 20β-hydroxy steroids. This mixture can be separated by chromatography or fractional crystallization, or it can be used without further purification as the starting material for the process of this invention according to variation (a).

It is also possible to produce the D-homo steroids of general Formula I from compounds of general Formula III by reacting the latter in an alcohol with the amount required for the reaction of an oxidizing heavy metal salt, e.g., silver oxide, lead (IV) oxide, minimum (red lead oxide), vanadium (V) oxide, or active manganese (IV) oxide. However, the yields of desired process product obtained with this reaction normally are extremely unsatisfactory. Surprisingly, better yields of these products are obtained if the compounds of general Formula III or their hydrates or hemiacetals are oxidized with atmospheric oxygen or with active manganese (IV) oxide in an alcohol which contains cyanide ions and has been buffered to a pH of 4-7.

The yields can additionally be improved by conducting the oxidation under the above-mentioned conditions in the presence of a dipolar aprotic solvent.

This preferred embodiment of process variant (b) can be accomplished, for example, as follows:

Atmospheric oxygen or active manganese (IV) oxide as customarily employed for oxidation reactions is utilized for this variation of the process (L. F. Fieser and M. Fieser, Reagents for Organic Synthesis; John Wiley and Sons, Inc., New York - London - Sidney (1967) 637 et seq.).

For this process variation, preferred alcohols are primary or secondary aliphatic or cycloaliphatic alcohols of 1-12 carbon atoms, such as, for example, methanol, ethanol, propanol, hexanol, cyclohexanol, isopropyl alcohol, butanol, butan-2-ol, pentanol, benzyl alcohol and octanol.

This reaction is conducted using cyanide ions as the catalyst. Reagents yielding cyanide ions are preferably alkali cyanides, e.g., sodium or potassium cyanide. Preferably, 0.01 mole to 10 moles and especially 0.1-1.0 mole of cyanide is utilized per mole of compound III. When using alkali cyanides as the reagents yielding cyanide ions, the reaction is conducted by further adding to the reaction mixture the amount of mineral acids such as, for example, sulfuric acid, phosphoric acid, or hydrogen chloride, required to buffer the alkali cyanide or adding for the same purpose sulfonic acid, e.g., p-toluenesulfonic acid or carboxylic acid, e.g., formic acid or acetic acid.

This reaction is preferably conducted in the presence of a dipolar aprotic solvent. Suitable dipolar aprotic solvents are, for example: dimethylformamide, N-methylacetamide, dimethylacetamide, N-methylpyrrolidone, dimethyl sulfoxide, sulfolane, dimethylsulfone, hexamethylphosphoric triamide, or an n-alkyl cyanide of 1-5 carbon atoms in the alkyl group, for example, acetonitrile.

The reaction is suitably conducted using as the reaction solvent, 2-200 ml. per gram of compound III of a mixture consisting of 5-50% of a lower alcohol and 50-95% of a dipolar aprotic solvent.

The process is effected advantageously at a reaction temperature of from −20° to +100° C. and preferably at a reaction temperature of from 0° to =50° C. The reaction time is dependent on the reaction temperature and the selection of the reactants. Usually, when using atmospheric oxygen, this reaction time is 5-120 minutes and, when using active manganese (IV) oxide, 1-30 minutes.

The starting compounds of general Formula III can be produced in a conventional manner, for example, by reacting the corresponding 21-hydroxy steroids for 20-120 minutes with copper (II) acetate and atmospheric oxygen in a lower primary alcohol of 1-4 carbon atoms at room temperature. During this reaction, mixtures of the free aldehydes and their hemiacetals are formed which can be used without further purification as starting substances for the process of this invention.

The 21-aldehydes of Formula III and the corresponding 21-hydroxy and 21-alkoxy-D-homo steroids are claimed in our concurrently filed application Ser. No. 609,706, filed Sept. 2, 1975, whose disclosure is incorporated by reference.

The process of this invention according to variations (c), (d), and (e), as well as the optional subsequent reactions can be conducted, for example, under the conditions described in German Unexamined Laid-Open Application DOS 2,264,003 and U.S. Application Ser. No. 426,702 filed Dec. 20, 1973, now U.S.

Pat. No. 3,919,421 whose disclosure is incorporated by reference.

The starting compounds for the process of this invention are produced according to methods generally known to one skilled in the art and will be explained in greater detail below, using as examples typical representatives thereof.

Examples of D-homo steroids of the general Formula I which can be prepared employing the processes of this invention are:

11β-hydroxy-3,20-dioxo-D-homo-1,4-pregnadien-21-oic acid
11β,17aα-dihydroxy-3,20-dioxo-D-homo-1,4-pregnadien-21-oic acid
6α-fluoro-11β-hydroxy-3,20-dioxo-D-homo-1,4-pregnadien-21-oic acid
6α-fluoro-11β,17aα-dihydroxy-3,20-dioxo-D-homo-1,4-pregnadien-21-oic acid
9α-fluoro-11β-hydroxy-3,20-dioxo-D-homo-1,4-pregnadien-21-oic acid
9α-fluoro-11β, 17aα-dihydroxy-3,20-dioxo-D-homo-1,4-pregnadien-21-oic acid
9α-chloro-11β-hydroxy-3,20-dioxo-D-homo-1,4-pregnadien-21-oic acid
9α-chloro-11β, 17aα-dihydroxy-3,20-dioxo-D-homo-1,4-pregnadien-21-oic acid
11β-fluoro-9α-chloro-3,20-dioxo-D-homo-1,4-pregnadien-21-oic acid
11β-fluoro-9α-chloro-17aα-hydroxy-3,20-dioxo-D-homo-1,4-pregnadien-21-oic acid
9α, 11β-dichloro-3,20-dioxo-D-homo-1,4-pregnadien-21-oic acid
9α, 11β-dichloro-17aα-hydroxy-3,20-dioxo-D-homo-1,4-pregnadien-21-oic acid
11β-hydroxy-3,20-dioxo-6α-methyl-D-homo-1,4-pregnadien-21-oic acid
11β,17aα-dihydroxy-3,20-dioxo-6α-methyl-D-homo-1,4-pregnadien-21-oic acid
11β-hydroxy-3,20-dioxo-6α,17α-dimethyl-D-homo-1,4-pregnadien-21-oic acid
11β, 17aα-dihydroxy-3,20-dioxo-6α,17α-dimethyl-D-homo-1,4-pregnadien-21-oic acid
6α-fluoro-11β-hydroxy-3,20-dioxo-17α-methyl-D-homo-1,4-pregnadien-21-oic acid
6α-fluoro-11β,17aα-dihydroxy-3,20-dioxo-17α-methyl-D-homo-1,4-pregnadien-21-oic acid
9α-fluoro-11β-hydroxy-3,20-dioxo-17α-methyl-D-homo-1,4-pregnadien-21-oic acid
9α-fluoro-11β,17aα-dihydroxy-3,20-dioxo-17α-methyl-D-homo-1,4-pregnadien-21-oic acid
6α,9α-difluoro-11β-hydroxy-3,20-dioxo-17α-methyl-D-homo-1,4-pregnadien-21-oic acid
6α,9α-difluoro-11β, 17aα-dihydroxy-3,20-dioxo-17α-methyl-D-homo-1,4-pregnadien-21-oic acid
6α-fluoro-9α-chloro-11β-hydroxy-3,20-dioxo-17α-methyl-D-homo-1,4-pregnadien-21-oic acid
6α-fluoro-9α-chloro-11β,17aα-dihydroxy-3,20-dioxo-17α-methyl-D-homo-1,4-pregnadien-21-oic acid, as well as the methyl, ethyl, aminoethyl, 2-methoxyethyl, propyl, propenyl, 3-hydroxypropyl, isopropyl, butyl, isobutyl, sec.-butyl, tert.-butyl, amyl, isoamyl, 2-methylbutyl, cyclopentyl, hexyl, cyclohexyl, heptyl, benzyl, menthyl, octyl, and decyl esters of these acids, and the D-homo-4-pregnenes corresponding to each of the above and the 17aα- acetoxy esters corresponding to each of the above 17aα- hydroxy compounds.

The novel D-homo steroids of this invention are pharmacologically active compounds distinguished particularly in that they possess a pronounced topical anti-inflammatory activity and are practically inactive systemically. Moreover, these D-homo steroids are often distinguished by a rapid onset of effectiveness, a high intensity of effectiveness, and a long duration of activity. They have a favorable resorbability and, in galenic preparations, a relatively good stability. The D-homo steroids of general Formula I are metabolized in the body differently than the conventional corticoids with anti-inflammatory effectiveness.

The novel compounds are suitable in combination with the vehicles customary in galenic pharmacy for the local treatment of contact dermatitis, eczema of a great variety of types, neurodermatoses, erythrodermia, burns, pruritus vulvae et ani, rosacea, erythematodes cutaneus, psoriasis, lichen ruber planue et verrucosus, and similar skin diseases.

The special drug preparations are produced in the usual manner by converting the effective agents with suitable additives into the desired form of application, e.g., solutions, lotions, ointments, creams, or plasters. In the thus-formulated medicinal agents, the concentration of active agent is dependent on the form of administration. In case of lotions and ointments, an effective agent concentration of 0.001 to 1% is preferably employed.

Moreover, the novel compounds are also suitable for the production of inhalants, optionally in combination with the usual vehicles and auxiliary agents.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

EXAMPLE 1 a. 130 ml. of methyl iodide is added dropwise to 45 g. of magnesium filings in 1400 ml. of absolute ether. After the magnesium has been dissolved, 2500 ml. of absolute tetrahydrofuran is gradually added thereto, and the mixture is distilled until the distillate has reached a boiling point of 55° C. Then the mixture is cooled to 20° C., 7 g. of copper (I) chloride and a solution of 100 g. of 3β-acetoxy-D-homo-5,17( a)-dien-20-one in 1000 ml. of absolute tetrahydrofuran are added thereto, and the mixture is stirred for 40 minutes at 20° C.

Thereafter, the mixture is cooled to 0° C,; 230 ml. of 2N sulfuric acid is added dropwise thereto and the mixture is subsequently extracted with ethyl acetate. The extract is washed with sodium thiosulfate solution and water, dried over sodium sulfate, and concentrated under vacuum.

The thus-obtained residue is combined under heating with 300 ml. of pyridine and 150 ml. of acetic anhydride, and the thus-obtained solution is allowed to stand for 16 hours at room temperature. Then, the mixture is poured into ice water, the thus-precipitated product is vacuum-filtered and dissolved in methylene chloride. The methylene chloride solution is washed with dilute sulfuric acid and water, concentrated under vacuum, and the residue is recrystallized from methylene chloride-ethyl acetate. Yield: 75.6 g. of 3β- acetoxy-17α-methyl-D-homo-5-pregnen-20-one, m.p. 212°–213° C.

b. 30 g. of 3β-acetoxy-17α-methyl-D-homo-5-pregnen-20-one is combined with 300 ml. of glacial acetic acid and heated to 40°–45° C. Within 10 minutes, a solution of 7.9 ml. of bromine in 60 ml. of glacial acetic acid is then added dropwise to the mixture. The latter is allowed to cool, poured into ice-cold potassium acetate solution, the thus-precipitated product is vacuum-filtered, the latter dissolved in ethyl acetate, the ethyl acetate phase is washed with water, evaporated under vacuum at a bath temperature of 40° C. to dryness, and the thus-obtained crude product is 5,6,21-tribromo-3β-acetoxy-17α-methyl-D-homo-pregnan-20 one.

c. The thus-obtained crude product is combined with 800 ml. of acetone and 80 g. of sodium iodide and stirred under darkness for 16 hours at 20° C. Subsequently the reaction mixture is combined with ice-cold sodium thiosulfate solution; the thus-separated iodide is filtered off, dissolved in ethyl acetate, the ethyl acetate phase is washed with water and concentrated under vacuum.

d. The residue thus produced is dissolved in 420 ml. of dimethylformamide, mixed with 24 ml. of glacial acetic acid and 42 ml. of triethylamine, and agitated for 4.5 hours under nitrogen at 110° C. Subsequently the reaction mixture is allowed to cool to room temperature, poured into ice-cold sodium chloride solution, and the thus-precipitated product is filtered and dissolved in methylene chloride. The methylene chloride solution is washed with water, dried over sodium sulfate, concentrated under vacuum, and the residue is purified by chromatography over a silica gel column. Yield: 19.5 g. of 3β,21-diacetoxy-17α-methyl-D-homo-5-pregnen-20-one which melts, after recrystallization from ether-pentane, at 135.5°–137.5° C.

e. 24.4 g. of 3β,21-diacetoxy-17α-methyl-D-homo-5-pregnen-20-one is dissolved in 250 ml. of methylene chloride, mixed with 250 ml. of 1% methanolic potassium hydroxide solution, and refluxed for 25 minutes. Then, 3 ml. of glacial acetic acid is added to the reaction mixture, the latter is concentrated under vacuum, the residue is taken up in tetrahydrofuran, and the thus-produced solution is concentrated under vacuum. The residue is recrystallized from acetone, thus obtaining 15.8 g. of 3β,21-dihydroxy-17α-methyl-D-homo-5-pregnen-20-one, m.p. 198°–202° C.

f. 11.7 g. of 3β,21-dihydroxy-17α-methyl-D-homo-5-pregnen-20-one is combined with 150 ml. of dimethylformamide, 20 ml. of acetic anhydride, and 1.1 g. of lead diacetate, and the mixture is agitated for 90 minutes at room temperature. The mixture is then poured into ice-cold sodium chloride solution; the thus-separated product is vacuum-filtered and dissolved in methylene chloride. The methylene chloride extract is washed with water, dried, and concentrated under vacuum. The product thus obtained is recrystallized from methylene chloride-diisopropyl ether, yielding 11.6 g. of 3β-hydroxy-21-acetoxy-17α-methyl-D-homo-5-pregnen-20-one, m.p. 188.5°–191° C.

g. 20.5 g. of 3β-hydroxy-21-acetoxy-17α-methyl-D-homo-5-pregnen-20-one is combined with 500 ml. of toluene and 20 ml. of cyclohexanone and heated to the boiling point until several milliliters have been distilled off. Then, a solution of 4.4 g. of aluminum isopropylate in 50 ml. of toluene is added to the mixture; the latter is heated for another hour to such an extent that always some solvent is being distilled off.

The reaction mixture is allowed to cool, diluted with ethyl acetate, the ethyl acetate phase is washed with 1N sulfuric acid and water, and concentrated under vacuum. The residue is purified by chromatography over a silica gel column, recrystallized from acetone-hexane, and the yield is 15.7 g. of 21-actoxy-17α-methyl-D-homo-4-pregnene-3,20-dione, m.p. 200.5°–202° C.

h. A 2-liter Erlenmeyer flask, containing 500 ml. of a nutrient solution, sterilized in an autoclave for 30 minutes at 120° C., made up of 1% of corn steep liquid, 1% of pulverized soybeans, and 0.005% of soybean oil, set to pH 6.2, is inoculated with a lyophilized culture of Curvularia lunata (NRRL 2380) and shaken on a rotary vibrator for 72 hours at 30° C. This subculture is utilized for inoculating a 20-liter fermentor made of stainless steel and filled with 15. l. of a medium, sterilized at 121° C. and 1.1 atmospheres gauge, of 1% of corn steep liquor, 0.5% of glucose, and 0.005% of soybean oil, set to pH 6.2. While adding Silicone SH as antifoam agent, the culture is cultivated for 24 hours at 29° C. under aeration (10 l./min.), a pressure of 0.7 atmosphere gauge, and under agitation (220 r.p.m.). One liter of the culture broth is transferred under sterile conditions into 14 liters of a medium sterilized as above and consisting of 1% of corn steep liquor, 1.25% of pulverized soybeans, and 0.005% of soybean oil and grown under the same conditions. After 6 hours, a solution of 3g. of 21-acetoxy-17α-methyl-D-homo-4-pregnene-3,20-dione in 150 ml. of dimethylformamide is added thereto.

After a contact time of 23 hours, the content of the fermentor is extracted twice with respectivelly 10 l. of methyl isobutyl ketone, and the extract is evaporated under vacuum at a bath temperature of 50° C. The residue is washed repeatedly with hexane to remove the silicone oil, and then recrystallized from ethyl acetate while adding activated carbon, thus obtaining 608 mg. of pure 11β,21-dihydroxy-17α-methyl-D-homo-4-pregnene-3,20-dione, m.p. 200.3° C.

i. A 2-liter Erlenmeyer flask containing 500 ml. of a nutrient solution, sterilized for 30 minutes in an autoclave at 120° C., made up of 1.5% of peptone, 1.2% of corn steep liquor, and 0.2% of MgSO$_4$, set to pH 6.5, is inoculated with a lyophilized culture of Bacillus lentus (ATCC 13 805) and shaken for 24 hours at 30° C. This subculture is then used to inoculate a 20-liter fermentor of stainless steel, containing 15 l. of a liquid nutrient medium, sterilized at 121° C. and 1.1 atmospheres gauge, of 0.2% of yeast extract, 1% of corn steep liquor, and 0.1% of glucose, set to pH 7.0. While adding Silicone SH as the antifoam agent, the mixture is grown at 29° C. under aeration and agitation. After a growth phase of 6 hours, a solution of 3 g. of 11β,21-dihydroxy-17α-methyl-D-homo-4-pregnene-3,20dione in 150 ml. of dimethylformamide is added thereto.

After a contact time of 15 hours, the content of the fermentor is extracted twice with respectively 10 l. of methyl isobutyl ketone, and the extract is concentrated under vacuum. The residue is washed with hexane to remove the silicone oil and then recrystallized from acetone-diisopropyl ether in the presence of activated carbon. Yield: 2.2 g. of 11β,21-dihydroxy-17α-methyl-D-homo-1,4-pregnadiene-3,20-dione, m.p. 159° C.

j. One gram of 11β,21-dihydroxy-17α-methyl-D-homo-1,4-pregnadiene-3,20-dione is combined with 250 ml. of methanol and 300 mg. of copper (II) acetate and agitated for 30 minutes while passing air through the mixture. Then, the latter is diluted with methylene chlorine, the methylene chloride phase is washed with ammonium chloride solution and water, concentrated under vacuum, and 1.1 g. of 11β-hydroxy-3,20-dioxo-17α-methyl-D-homo-1,4-pregnadien-21-al is obtained as the crude product.

k. The thus-produced aldehyde is dissolved in 50 ml. of methanol, combined with 160 mg. of potassium cyanide, 1 ml. of glacial acetic acid, and 2 g. of active manganese (IV) oxide, and stirred for 30 minutes at 20° C. The inorganic substance is then removed by vacuum-filtering, mixed with methylene chloride, the filtrates washed with water, concentrated under vacuum, the residue chromatographed over a silica gel column, and the product thus obtained is the methyl ester of 11β-hydroxy-3,20-dioxo-17α-methyl-D-homo-1,4-pregnadien-21-oic acid, m.p. 172°–174° C. (from hexane-acetone).

EXAMPLE 2 a. A 2-liter Erlenmeyer flask containing 500 ml. of a nutrient solution, sterilized for 30 minutes in an autoclave at 120° C., made up of 1% of corn steep liquor, 1% of pulverized soybeans, and 0.005% of soybean oil, set to pH 6.2, is inoculated with a lyophilized culture of Curvularia lunata (NRRL 2300) and shaken for 72 hours at 30° C. on a rotary vibrator. This subculture is then employed to inoculate a 20-liter fermentor containing 15 l. of a medium, sterilized at 121° C. and 1.1 atmospheres gauge, made up of 1% of corn steep liquor, 0.5% of glucose, and 0.005% of soybean oil, set to pH 6.2. Under the addition of Silicone SH as the antifoam agent, the culture is cultivated at 29° C. under aeration (10 l./min.) a pressure of 0.7 atmospheres gauge, and under agitation (220 r.p.m.) for 24 hours. One liter of the culture broth is transferred under sterile conditions into 14 l. of a medium sterilized as above and consisting of 1% of corn steep liquor, 1.25% of pulverized soybeans, and 0.005% of soybean oil, and is grown under the same conditions. After 6 hours, a solution of 6 g. of 21-acetoxy-D-homo-4-pregnene-3,20-dione in 300 ml. of dimethyl sulfoxide is added thereto.

After a contact time of 44 hours, the content of the fermentor is extracted under agitation twice with respectively 10 l. of methyl isobutyl ketone, and the extract is evaporated under vacuum at a bath temperature of 50° C. The residue is once again washed with hexane to remove the silicone oil and then converted by digestion with acetone-isopropyl ether into a crystalline crude product (3.1 g.) which is used in this form for the subsequent dehydrogenation.

A sample of the crude product is recrystallized from acetone-ether to obtain 11β,21-dihydroxy-D-homo-4-pregnene-3,20-dione, m.p. 188/191°–195° C.

b. A 2-liter Erlenmeyer flask containing 500 ml. of a nutrient solution, sterilized for 30 minutes at 120° C. in an autoclave and made up of 1.5% of peptone, 1.2% of corn steep liquor, and 0.2% of MgSO$_4$, set to pH 6.5, is inoculated with a lyophilized culture of Bacillus lentus (ATCC 13 805) and shaken for 24 hours at 30° C. This subculture is then used to inoculate a 20-liter fermentor containing 15 l. of a liquid nutrient medium, sterilized at 121° C. and 1.1 atmospheres gauge, made up of 0.2% of yeast extract, 1% of corn steep liqour, and 0.1% of glucose, set to pH 7.0. With the addition of Silicone SH as the antifoam agent, the culture is grown at 29° C. under aeration and agitation. After a growth phase of 6 hours, a solution of 6 g. of 11β,21-dihydroxy-D-homo-4-pregnene-3,20-dione in 100 ml. of dimethylformamide is added thereto.

After a contact time of 42 hours, the content of the fermentor is extracted twice with respectively 10 l. of methyl isobutyl ketone, and the extract is evaporated under vacuum. The residue is washed with hexane to remove the silicone oil and, after treatment with active C in methanolic solution, recrystallized twice from acetone-ether to obtain 3 g. of 11β,21-dihydroxy-D-homo-1,4-pregnadiene-3,20-dione, m.p. 170/173°–174° C.

c. 800 mg. of 11β,21-dihydroxy-D-homo-1,4-pregnadiene-3,20-dione is dissolved in 8 ml. of dimethylformamide, combined with 1.6 ml. of acetic ahydride and 112 mg. of lead diacetate, and agitated for 2 hours at room temperature. Then, the mixture is precipitated into ice water, the product is vacuum-filtered, washed with water, and dried. Recrystallization from acetone-hexane yields 820 mg. of 11β-hydroxy-21-acetoxy-D-homo-1,4-pregnadiene-3,20-dione, m.p. 192°–193° C.

d. 760 mg. of 11β-hydroxy-21-acetoxy-D-homo-1,4-pregnadiene-3,20-dione is dissolved in 4 ml. of dimethylformamide and 0.76 ml. of pyridine, and 0.38 ml. of methanesulfonic acid chloride is added dropwise thereto. The mixture is thereafter stirred for 1.5 hours at 80° C., then cooled to 20° C., poured into ice water, and the thus-precipitated product is vacuum-filtered, washed with water, and dried under vacuum. After recrystallization from acetone-hexane, the yield is 650 mg. of 21-acetoxy-D-homo-1,4,9(11)-pregnatriene-3,20-dione, m.p. 135°–136° C.

e. 374 mg. of 21-acetoxy-D-homo-1,4,9(11)-pregnatriene-3,20-dione is dissolved in 9 ml. of tetrahydrofuran; 535 mg. of N-bromosuccinimide is added thereto, the mixture is cooled to 0°–5° C., and 3.3 ml. of 1N perchloric acid is added dropwise. The mixture is then stirred for 30 minutes at 20° C., poured into ice-cold sodium sulfite solution, the precipitated product is vacuum-filtered and dissolved in methylene chloride. The methylene chloride solution is washed with water and concentrated under vacuum, thus obtaining 520 mg. of crude 21-acetoxy-9α-bromo-11β-hydroxy-D-homo-1,4-pregnadiene-3,20-dione.

f. 520 mg. of the crude bromohydrin is heated in 25 ml. of ethanol with 1.25 g. of potassium acetate for 1 hour under reflux. The reaction mixture is poured into ice water, the thus-precipitated product is vacuum-filtered, washed with water, and dried under vacuum. After recrystallization from cyclohexane, 320 mg. of 21-acetoxy-9β,11β-epoxy-D-homo-1,4-pregnadiene-3,20-dione is obtained, m.p. 152–153° C.

g. 320 mg. of 21-acetoxy-9β,11β-epoxy-D-homo-1,4-pregnadiene-3,20-dione is dissolved in 2 ml. of dimethylformamide and added to a mixture of 2 ml. of dimethylformamide and 2 ml. of hydrogen fluoride, cooled to −20° C. The mixture is stirred for 19 hours at room temperature and then poured into water which contains potassium acetate. The precipitated product is vacuum-filtered, washed with water, dried, and recrystallization from acetone yields 169 mg. of 9α-fluoro-11β-hydroxy-21-acetoxy-D-homo-1,4-pregnadiene-3,20-dione, m.p. 227°–228° C.

h. Three grams of 9α-fluoro-11β-hydroxy-21-acetoxy-D-homo-1,4-pregnadiene-3,20-dione is combined with 12 ml. of methanol and 12 ml. of methylene chloride, cooled to −5° C., and a solution of 0.18 g. of potassium hydroxide in 6 ml. of methanol is added dropwise thereto. The mixture is then stirred for another 60 minutes at 0° C., neutralized with acetic acid, diluted with methylene chloride, the methylene chloride phase washed with water, concentrated under vacuum, and the residue is recrystallized from hexane-acetone, thus obtaining 2.4 g. of 9 α -fluoro-11β,21-dihydroxy-D-homo-1,4-pregnadiene-3,20-dione, m.p. 197°–100° C.

i. Under the conditions of Example 1(j), one gram of 9α-fluoro-11β,21-dihydroxy-D-homo-1,4-pregnadiene-3,20-dione is reacted, yielding 1.1 g. of 9α-fluoro-11β-hydroxy-3,20-dioxo-D-homo-1,4-pregnadien-21-al as the crude product.

j. Under the conditions of Example 1(k), but with the use of butanol in place of methanol, one gram of 9α-fluoro-11β-hydroxy-3,20-dioxo-D-homo-1,4-pregnadien-21-al is reacted, yielding the butyl ester of 9α-fluoro-11β-hydroxy-3,20-dioxo-D-homo-1,4-pregnadien-21-oic acid, m.p. 121°–123° C.

EXAMPLE 3 a. 11β,21-Dihydroxy-D-homo-1,4-pregnadiene-3,20-dione is reacted under the conditions of Example 1(j), thus obtaining 11β-hydroxy-D-homo-1,4-pregnadien-21-al as the crude product.

b. The thus-obtained aldehyde is reacted under the conditions of Example 2(j), obtaining the butyl ester of 11β-hydroxy-3,20-dioxo-D-homo-1,4-pregnadien-21-oic acid, m.p. 103°–104.5° C.

EXAMPLE 4 a. A Grignard solution (prepared from 21 g. of magnesium filings, 72.5 g. of methyl iodide, and 1000 ml. of ether) is diluted with 1000 ml. of absolute tetrahydrofuran and distilled until the distillate has reached a boiling point of 50° C. The thus-obtained suspension is then cooled to 20° C., combined with 4 g. of copper(I) chloride and a solution of 50 g. of 3β-hydroxy-D-homo-5,17(17a)-pregnadien-20-one in 2000 ml. of absolute tetrahydrofuran, and the mixture is agitated for 20 minutes at room temperature. The reaction mixture is worked up as usual, the crude product is recrystallized from acetone, and the yield is 32.5 g. of 3β-hydroxy-17α-methyl-D-homo-5-pregnen-20-one, m.p. 207°–209° C.

b. 10 g. of 3β-hydroxy-17α-methyl-D-homo-5-pregnen-20-one is suspended in 1000 ml. of tetrahydrofuran and combined dropwise with a solution of 3.6 ml. of bromine in 10 ml. of glacial acetic acid (duration about 15 minutes). Subsequently, the reaction mixture is worked up as described in Example 1(b), thus obtaining 3β-hydroxy-5,6,21-tribromo-17α-methyl-D-homo-pregnan-20-one as a crude product.

c. The thus-obtained tribromo derivative is reacted under the conditions described in Example 1(c) with 300 ml. of acetone and 35 g. of sodium iodide and then worked up, obtaining the 21-iodide compound as the crude product.

d. The 21-iodide is dissolved in 140 ml. of dimethylformamide, combined with 8 ml. of glacial acetic acid and 14 ml. of triethylamine, and stirred for 11 hours at 90° C. The reaction mixture is worked up as described in Example 1 (d), thus obtaining 4.4 g. of 3β-hydroxy-21-acetoxy-17α-methyl-D-homo-5-pregnen-20-one, melting at 188°–190° C. after recrystallization from methylene chloride-diisopropyl ether.

e. 470 mg. of N-bromosuccinimide is introduced into a solution, cooled to −30° C., of 3 ml. of hydrogen fluoride and 3 ml. of dimethylformamide. Then, a precooled solution of 1 g. of 3β-hydroxy-21-acetoxy-17α-methyl-D-homo-5-pregnen-20-one in 8 ml. of methylene chloride is added to the mixture in incremental portions; the mixture is stirred for 10 minutes at −30° C., poured into ice-cold potassium bicarbonate solution, and extracted with methylene chloride. The methylene chloride phase is washed with water, evaporated to dryness under vacuum, the residue recrystallized from acetone, and the yield is 627 mg. of 6β-fluoro-5α-bromo-3β-hydroxy-21-acetoxy-17α-methyl-D-homo-5α-pregnan-20-one, m.p. 168.5° C. (decomposition).

f. 300 mg. of 6β-fluoro-5α-bromo-3β-hydroxy-21-acetoxy-17α-methyl-D-homo-5α-pregnan-20-one is combined, in 10 ml. of acetone, dropwise with 0.19 ml. of Jones reagent (containing, per liter, 267 g. of chromium (VI) oxide, 230 ml. of concentrated sulfuric acid in water); the mixture is agitated for 10 minutes at 20° C. Thereafter, the mixture is poured into ice water, the separated product is vacuum-filtered, taken up in methylene chloride, the methylene chloride phase is washed with water and concentrated under vacuum. Yield: 298 mg. of 6β-fluoro-5α-bromo-21-acetoxy-17α-methyl-D-homo-5α-pregnane-3,20-dione as the crude product.

g. This crude product is dissolved in 5 ml. of glacial acetic acid and agitated for 3 hours at 30° C. Then, the mixture is combined with 100 mg. of sodium acetate, stirred for 10 minutes at 30° C., poured into ice water; the thus-separated product is vacuum-filtered and taken up in methylene chloride. The methylene chloride phase is washed with water, concentrated under vacuum, and the residue is recrystallized from acetone, thus obtaining 250 mg. of 6α-fluoro-21-acetoxy-17α-methyl-D-homo-4-pregnene-3,20-dione.

h. Under the conditions described in Example 1(h), 3 g. of 6α-fluoro-21-acetoxy-17α-methyl-D-homo-4-pregnene-3,20-dione is fermented with Curvularia lunata, worked up, and the product is 6α-fluoro-11β,21-dihydroxy-17α -methyl-D-homo-4-pregnene-3,20-dione.

i. Under the conditions described in Example 1(i), 1.2 g. of 6α-fluoro-11β,21-dihydroxy-17α-methyl-D-homo-4-pregnene-3,20-dione is reacted with a culture of Bacillus lentus, worked up, and the product is 6α-fluoro-11β,21-dihydroxy-17α-methyl-D-homo-1,4-pregnadiene-3,20-dione.

j. Under the conditions of Example 1(j), 6α-fluoro-11β,21-dihydroxy-17α-methyl-D-homo-1,4-pregnadiene-3,20-dione is reacted, thus obtaining 6α-fluoro-11β-hydroxy-3,20-dioxo-17α-methyl-D-homo-1,4-pregnadien-21-al as a crude product.

k. Under the conditions of Example 2(j), 6α-fluoro-11β-hydroxy-3,20-dioxo-17α-methyl-D-homo-1,4-pregnadien-21-al is reacted, yielding the butyl ester of 6α-fluoro-11β-hydroxy-3,20-dioxo-17α-methyl-D-homo-1,4-pregnadien-21-oic acid.

EXAMPLE 5 a. One gram of 17aα,21-dihydroxy-D-homo-4-pregnene-3,20-dione (DOS 2,314,592) is dissolved in 200 ml. of methanol and combined with 250 mg. of copper-(II) acetate. For 50 minutes, air is conducted through the mixture; then the latter is stirred into water and extracted with methylene chloride. The methylene chloride phase is washed, dried, concentrated under vacuum, and the product is 1.03 g. of 179α-hydroxy-3,20-dioxo-D-homo-4-pregnen-21-al in crude form.

b. 510 mg. of the thus-produced aldehyde is dissolved in 18.3 ml. of chloroform and 11.5 ml. of methanol, combined with 0.63 ml. of glacial acetic acid and 115 mg. of potassium cyanide, and agitated for 50 minutes at 20° C. The mixture is then diluted with methylene chloride, the methylene chloride phase is washed, concentrated under vacuum, and the residue chromatographed over a silica gel column, yielding 157 mg. of the methyl ester of 17,9α-hydroxy-3,20-dioxo-D-homo-4-pregnen-21-oic acid, m.p. 171°-172° C. (from hexane-acetone).

EXAMPLE 6 a. One gram of 11β,17aα,21-trihydroxy-D-homo-1,4-pregnadiene-3,20-dione is dissolved in 20 ml. of methanol and combined with 300 mg. of copper(II) acetate. Under agitation, air is conducted through the mixture for 2 hours, diluted with 200 ml. of chloroform, the chloroform phase is washed and concentrated under vacuum, and the crude product thus obtained is 11β,17aα-dihydroxy-D-homo-1,4-pregnadien-21-al which melts at 136°-140° C. after recrystallization from methanol.

b. The thus-prepared aldehyde is dissolved in 8 ml. of absolute methanol and 75 ml. of absolute acetonitrile, the solution is combined, in succession, with 3 g. of anhydrous calcium carbonate, 1.6 ml. of glacial acetic acid, 2 g. of active manganese (IV) oxide, and 0.352 g. of potassium cyanide. The mixture is agitated for 3 minutes at room temperature, then vacuum-filtered by way of a sinter vacuum filter into 300 ml. of ice water, and the residue is washed with chloroform. The organic phase is separated, the aqueous phase is extracted with chloroform, the chloroform phases are combined, washed, and concentrated under vacuum. The residue is chromatographed over silica gel, thus obtaining 570 mg. of the butyl ester of 11β,17aα-dihydroxy-3,20-dioxo-D-homo-1,4-pregnadien-21-oic acid, m.p. 110°-115° C. (from diisopropyl ether).

EXAMPLE 7

5.6 g. of 11β,21-dihydroxy-17α-methyl-D-homo-1,4-pregnadiene-3,20-dione is dissolved in 300 ml. of absolute methanol, combined with a solution of 1.6 g. of copper(II) acetate in 200 ml. of methanol, and stirred for 200 hours at 20°-25° C. Thereafter, the mixture is concentrated under vacuum, precipitated into water, and extracted with methylene chloride. The organic phase is washed with ammonia and water, dried, and concentrated by evaporation. The thus-obtained 20-epimer mixture of the methyl ester of 11β,20-dihydroxy-17α-methyl-3-oxo-D-homo-1,4-pregnadien-21-oic acid is dissolved in 50 ml. of methylene chloride, combined with 30 g. of active manganese (IV) oxide, and heated to the boiling point for 6 hours. Then, the mixture is filtered off from the manganese oxide, the filtrate is concentrated, and the residue is chromatographed on silica gel. With hexane-acetone (9 + 1), the methyl ester of 11β-hydroxy-17α-methyl-3,20-dioxo-D-homo-1,4-pregnadien-21-oic acid is eluted and recrystallized from acetone-hexane; m.p. 172°-174° C.

EXAMPLE 8

13 g. of 6α-fluoro-11β,21-dihydroxy-17α-methyl-D-homo-1,4-pregnadiene-3,20-dione is combined in 1100 ml. of ethanol with 6.5 g. of copper(II) acetate and agitated for 7 days at 20°-25° C. The solution is concentrated under vacuum, diluted with methylene chloride, washed with ammonia and water, and evaporated. The crude product is dissolved in 400 ml. of acetone and cooled to 0°-5° C. and then combined dropwise with 26 ml. of Jones reagent. After a reaction time of 30 minutes, the mixture is stirred into water, the thus-precipitated product is vacuum-filtered and recrystallized from hexane-acetone, yielding 7.2 g. of 6α-fluoro-17α-methyl-3,11,20-trioxo-D-homo-1,4-pregnadien-21-oic acid ethyl ester, m.p. 118°-120° C.

EXAMPLE 9

1.16 g. of 11β,17aα-dihydroxy-3,20-dioxo-D-homo-1,4-pregnadien-21-al, crude product, is dissolved in 8 ml. of absolute methanol and 75 ml. of absolute acetonitrile; then, 3 g. of anhydrous calcium sulfate, 1.6 ml. of glacial acetic acid, 2 g. of manganese (IV) oxide, and 0.352 mg. of potassium cyanide are added in succession, and the mixture is stirred for 3 minutes at 20° C. The reaction mixture is vacuum-filtered by way of a sinter vacuum filter into 300 ml. of ice water; the residue is washed with chloroform, the organic phase is separated, and the aqueous phase is once more extracted with chloroform. The combined chloroform extracts are washed neutral with water, dried over sodium sulfate, and evaporated under vacuum.

The residue (0.97 g.) is chromatographed on silica gel. With 35-45% ethyl acetate-hexane, 570 mg. of the methyl ester of 11β,17aα-dihydroxy-3,20-dioxo-D-homo-1,4-pregnadien-21-oic acid is eluted and recrystallized from diisopropyl ether; m.p. 110°-115° C.

EXAMPLE 10

300 mg. of 11β,17aα-dihydroxy-3,20-dioxo-D-homo-1,4-pregnadien-21-al is dissolved in 7.5 ml. of acetonitrile and 2.4 ml. of n-propanol. In succession, 0.9 g. of anhydrous calcium sulfate, 0.48 ml. of glacial acetic acid, 0.6 g. of manganese (IV) oxide, and 0.105 g. of potassium cyanide are added thereto, and the mixture is stirred for 6 minutes at 20° C. The mixture is then worked up and chromatographed as described in Example 9. Recrystallization from ether-pentane yields 119 mg. of 11β,17aα-dihydroxy-3,20-dioxo-D-homo-1,4-pregnadien-21-oic acid propyl ester, m.p. 90°-95° C.

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A D-homo steroid of the formula

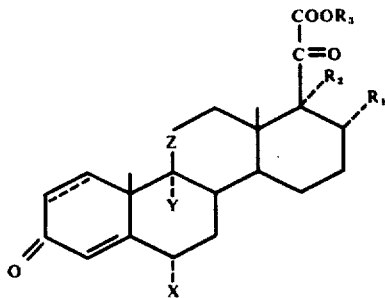

wherein ═ is a single bond or a double bond; X is a hydrogen atom, a fluorine atom, or methylene; Y is a hydrogen atom, a fluorine atom, or a chlorine atom; Z is methylene, carbonyl, β-hydroxymethylene, a β-n-alkanoyloxymethylene of 1–4 carbon atoms in the alkanoyl group or when Y is a chlorine atom, also β-fluoromethylene or β-chloromethylene; $R_1$ is a hydrogen atom or methyl; $R_2$ is a hydrogen atom, hydroxy or n-alkanoyloxy of 1–4 carbon atoms; and $R_3$ is a hydrogen atom or a sodium, potassium or ammonium ion, alkyl of 1–12 carbon atoms, cycloalkyl of 3–12 rng carbon atoms or hydrocarbon mono or di-cyclic aryl or aralkyl of up too 12 carbon atoms.

2. A compound of claim 1, wherein ═ is a double bond.
3. A compound of claim 1, wherein X is H.
4. A compound of claim 1, wherein Y is H.
5. A compound of claim 1, wherein Z is B-hydroxymethylene.
6. A compound of claim 1, wherein Y is Cl and Z is B-fluoromethylene or B-chloromethylene.
7. A compound of claim 1, wherein $R_2$ is H.
8. A compound of claim 1, wherein $R_3$ is alkyl of 1–4 carbon atoms.
9. 11β-Hydroxy-3,20-dioxo-17α-methyl-D-homo-1,4-pregnadien-21-oic acid methyl ester, a compound of claim 1.
10. 9α-Fluoro-11β-hydroxy-3,20-dioxo-D-homo-1,4-pregnadien-21-oic acid butyl ester, a compound of claim 1.
11. 11β-Hydroxy-3,20-dioxo-D-homo-1,4-pregnadien-21-oic acid butyl ester, a compound of claim 1.
12. 6α-Fluoro-11β-hydroxy-3,20-dioxo-17α-methyl-D-homo-1,4-pregnadien-21-oic acid butyl ester, a compound of claim 1.
13. 17aα-Hydroxy-3,20-dioxo-D-homo-4-pregnen-21-oic acid methyl ester, a compound of claim 1.
14. 11β,17aα-Dihydroxy-3,20-dioxo-D-homo-1,4-pregnadien-21-oic acid butyl ester, a compound of claim 1.
15. 6α-Fluoro-3,11,20-trioxo-17α-methyl-D-homo-1,4-pregnadien-21-oic acid ethyl ester, a compound of claim 1.
16. 11β,17aα-Dihydroxy-3,20-dioxo-D-homo-1,4-pregnadien-21-oic acid methyl ester, a compound of claim 1.
17. 11β,17aα-Dihydroxy-3,20-dioxo-D-homo-1,4-pregnadien-21-oic acid propyl ester, a compound of claim 1.
18. A compound of claim 1, wherein $R_3$ is alkyl of 1–8 carbon atoms.
19. A compound of claim 1, wherein $R_3$ is H.
20. A compound of claim 1, wherein $R_3$ is a sodium, potassium or ammonium ion.

* * * * *